United States Patent [19]

Barthelemy et al.

[11] Patent Number: 5,366,662
[45] Date of Patent: Nov. 22, 1994

[54] STABILIZED COMPOSITIONS COMPRISING HYDROFLUOROALKANES, PREMIXTURES INTENDED FOR THE PREPARATION OF POLYMERIC FOAMS AND POLYMERIC FOAMS OBTAINED BY THE USE THEREOF

[75] Inventors: Pierre Barthelemy, Pietrebais; Annie Leroy, Fauvillers, both of Belgium.

[73] Assignee: Solvay (Société Anonyme), Brussels,

[21] Appl. No.: 125,180

[22] Filed: Sep. 23, 1993

[30] Foreign Application Priority Data

Sep. 29, 1992 [BE] Belgium ............... 09200847

[51] Int. Cl.$^5$ .................................. C09K 3/00
[52] U.S. Cl. .................. 252/393; 252/394; 252/182.2; 521/113; 521/128; 521/131
[58] Field of Search ............ 252/393, 394, 182.2; 521/113, 128, 131

[56] References Cited

U.S. PATENT DOCUMENTS 5,169,996 12/1992 Crooker et al. .

FOREIGN PATENT DOCUMENTS

92/10453 6/1992 WIPO .

*Primary Examiner*—Morton Foelak
*Attorney, Agent, or Firm*—Spencer, Frank & Schneider

[57] ABSTRACT

Compositions comprising at least one hydrofluoroalkane and at least one stabilizing agent chosen from quinones and compounds containing a nitroso group, added in an amount sufficient to stabilize the hydrofluoroalkanes. These compositions can especially be used in premixtures for polyurethane foams.

7 Claims, No Drawings

STABILIZED COMPOSITIONS COMPRISING HYDROFLUOROALKANES, PREMIXTURES INTENDED FOR THE PREPARATION OF POLYMERIC FOAMS AND POLYMERIC FOAMS OBTAINED BY THE USE THEREOF

The present invention relates to stabilized compositions comprising at least one hydrofluoroalkane.

The entirely halogenated chlorofluorinated hydrocarbons (CFCs), suspected of having a harmful effect on the ozone layer, can be substituted in many applications, such as, for example, use as a blowing agent for the preparation of foams, as a heat-transfer fluid or as a propellant, by fluorinated hydrocarbons comprising at least one hydrogen atom, also called hydrofluoroalkanes (HFAs).

HFAs can degrade under certain conditions, so that their use in the fields mentioned above still poses a problem of stability.

Moreover, it is well known that polyurethane or polyisocyanurate foams can be prepared by reacting a polyisocyanate with a suitable amount of a polyol or a mixture of polyols, in the presence of a blowing agent consisting of a volatile liquid, which is vaporized by the heat released by the reaction between the isocyanate and the polyol. It is also well known that this reaction is promoted by the use of catalysts, such as amines or tin compounds, and that formation of the foam can be improved by addition of surface-active compounds. Other additives can also be used, such as, especially, flame-retardant agents.

It is common practise, in the field of polyurethane foams, to prepare premixtures of certain components used subsequently to prepare the foam. Usually, the appropriate amounts of polyol, blowing agent, catalyst, surfactant and flame-retardant agent are mixed to form a premixture. This premixture and the suitable amount of polyisocyanate are sold in two separate tanks. The final user has then only to mix the contents of the two tanks to manufacture the foam. Moreover, in the large foam production units, it is usual to store the mixture containing the polyol and the blowing agent. This liquid mixture has a lower viscosity than that of the pure polyol and is consequently easier to pump and to meter to the foam manufacturing area. Whatever the practice used, specific precautions must be taken. In fact, it has been observed that, in premixtures comprising polyols, the hydrofluoroalkane used as blowing agent is capable of degrading to various harmful degradation products. 1,1-Dichloro-1-fluoroethane, for example, degrades in the presence of polyols, especially to 1-chloro-1-fluoroethane, vinylidene chloride and vinylidene chlorofluoride. Hydracids can also be generated by this degradation.

A similar stability problem exists for solvent compositions obtained by mixing at least one HFA with various organic compounds, especially alcohols.

The subject of the present invention is to provide hydrofluoroalkane compositions of improved stability, more particularly against degradation induced by hydroxylated compounds.

The invention consequently relates to compositions comprising at least one hydrofluoroalkane and at least one stabilizing agent of the hydrofluoroalkane, characterized in that the stabilizing agent is chosen from quinones, compounds containing a nitroso group and their mixtures.

Hydrofluoroalkane is generally understood to denote any halogenated saturated hydrocarbon, of acyclic or alicyclic type, comprising at least one hydrogen atom and at least one fluorine atom. These hydrofluoroalkanes may or may not additionally comprise one or a number of chlorine or bromine atoms. Preferably, they do not comprise bromine. In a particularly preferred way, they comprise at least one chlorine atom.

Hydrofluoroalkanes which can be used in the compositions according to the invention are those which comprise from 1 to 6 carbon atoms and which correspond to the general formula $C_aH_bF_cX_d$ in which X is Cl and/or Br, preferably Cl, a is an integer from 1 to 6, b is an integer from 1 to 13, c is an integer from 1 to 13 and d is an integer from 0 to 8, with $b+c+d=2a+2$ when the hydrofluoroalkane is acyclic and with $b+c+d=2a$ when the hydrofluoroalkane is alicyclic. The compositions according to the invention particularly comprise acyclic hydrofluoroalkanes corresponding to the general formula above in which X is Cl, a is an integer from 1 to 4, b is an integer from 1 to 9, c is an integer from 1 to 9 and d is an integer from 0 to 5. More particularly, they comprise acyclic hydrofluoroalkanes corresponding to the general formula above in which X is Cl, a is an integer equal to 2 or 3, b is an integer from 1 to 6, c is an integer from 1 to 6 and d is an integer from 1 to 4. By way of examples, the hydrofluoroalkane of the compositions according to the invention can be selected from the compounds of crude formula $CHClF_2$, $CH_2F_2$, $CH_3CCl_2F$, $CH_3CClF_2$, $CH_3CHF_2$, $CH_3CF_3$, $CH_2FCH_2F$, $CH_2FCHF_2$, $CH_2FCF_3$, $CHF_2CCl_3$, $CHF_2CF_3$, $CHCl_2CF_3$, $CHF_2CHF_2$, $CF_3CHClF$, $CF_3CF_2CHCl_2$, $CF_2ClCF_2CHClF$, $CF_3CH_2CF_2CH_3$ and $CF_3CH_2CH_2CF_3$. 1,1-Dichloro-1-fluoroethane (HFA-141b) is preferred. Excellent results are obtained, especially when the compositions according to the invention are used as blowing agent in premixtures based on polyols, intended for the manufacture of polyurethane foams, very particularly when the hydrofluoroalkane is 1,1-dichloro-1-fluoroethane.

The stabilized compositions according to the invention can comprise a single hydrofluoroalkane or a mixture of different hydrofluoroalkanes.

Quinones which can be used in the compositions according to the invention can be unsubstituted or substituted by $C_1-C_{10}$ alkyl groups. When the quinones are substituted by alkyl groups, the latter are preferably branched. Examples of quinones which can be used to stabilize the compositions according to the invention especially comprise 1,4-benzoquinone, tetrahydro-1,4-benzoquinone, anthraquinone, tetrahydroanthraquinone or octahydroanthraquinone, optionally substituted by one or a number of $C_1-C_{10}$ alkyl groups. In particular, 1,4-benzoquinone, 2,6-dimethylbenzoquinone, 2-sec-amylanthraquinone, 2-tert-amylanthraquinone, 2-tert-amyltetrahydroanthraquinone or 2-tert-amyloctahydroanthraquinone is used. Very particularly, 1,4-benzoquinone, 2-tert-amyltetrahydroanthraquinone or 2-tert-amyloctahydroanthraquinone is used. Excellent results were obtained with 1,4-benzoquinone.

Compounds containing a nitroso group which can be used to stabilize the compositions according to the invention are acyclic, alicyclic, aromatic or heterocyclic compounds containing a nitroso (—N=O) group and optionally substituted by other groups, such as alkyl, amino or hydroxyl groups. By way of examples, there may be mentioned 2-methyl-2-nitrosopropane, nitrosobenzene, 2-nitrosotoluene, 3-nitrosodurene, 4-nitrosophenol, 1-nitroso-2-naphthol, 2-nitroso-1-naphthol, N-nitrosodimethylamine, N-nitrosodiethylamine, 4-nitrosodiphenylamine, N-nitrosodiethanolamine, 4-nitroso-N,N-dimethylaniline, 4-nitroso-N,N-diethylaniline, 1-nitrosopyrrolidine, N-nitrosomorpholine or 5-nitroso-2,4,6-triaminopyrimidine. 2-Methyl-2-nitrosopropane, 2-nitroso-1-naphthol or N-nitrosodiethylamine are more particularly chosen. Excellent results have been obtained with 2-methyl-2-nitrosopropane.

In the compositions according to the invention, the stabilizing agent must be used in an amount appropriate for stabilizing the hydrofluoroalkane. The optimum amount of stabilizing agent to be used depends on various parameters, among which figure especially the hydrofluoroalkane and the stabilizing agent selected. It can easily be determined in each specific case. In practice, there is generally used at least 0.01% by weight of each stabilizing agent with respect to the total weight of hydrofluoroalkane included in the composition. Preferably, at least 0.05% thereof is used. In a particularly preferred way, at least 0.1% thereof is used. Moreover, the amount by weight of each stabilizing agent with respect to the total weight of hydrofluoroalkane included in the composition does not generally exceed 10%. Preferably, it does not exceed 5%. In a particularly preferred way, it does not exceed 2%.

The compositions according to the invention can contain a number of stabilizing agents selected from quinones and compounds containing a nitroso group. Compositions according to the invention can consist essentially of the hydrofluoroalkane and stabilizing agent. As a variant, other stabilizing agents and/or other additives can also be added to the stabilized compositions according to the invention. The nature of the additives used depends mainly on the use for which the compositions according to the invention are intended.

The compositions according to the invention can advantageously be used as blowing agents for the preparation of polymeric foams. They can also be used as cleaning agents, for example as degreasing solvents for metal components. In this case, the additives are, for example, lower alcohols such as methanol, ethanol, propanol or isopropanol. They can also be used as heat-transfer fluids in refrigeration devices or as propellant gases for aerosol products.

The stabilized compositions according to the invention can in particular be used as blowing agents for the preparation of polyurethane or polyisocyanurate foams.

The invention also relates to premixtures intended for the preparation of polymeric foams, such as polyurethane or polyisocyanurate foams, comprising, as blowing agent, a composition comprising at least one hydrofluoroalkane and at least one stabilizing agent of the hydrofluoroalkane chosen from quinones and compounds containing a nitroso group.

The invention particularly relates to premixtures which comprise at least one polyol and which are intended for the manufacture of polyurethane foams. A large range of polyols, already disclosed in the prior art, can be used in these premixtures, such as polyether polyols and polyester polyols. The proportion of blowing agent with respect to the polyol in the premixtures will vary, especially according to the application, the type of foam prepared, the nature of the polyol, the nature of the hydrofluoroalkane included in the composition used as blowing agent and also according to other parameters. It can easily be determined in each specific case. In practice, there is generally used from 1 to 50 parts by weight of the composition comprising the hydrofluoroalkane and the stabilizing agent of the hydrofluoroalkane per 100 parts by weight of polyol. Excellent results have been obtained with premixtures comprising a polyol and 1,1-dichloro-1-fluoroethane stabilised according to the invention, intended for the manufacture of rigid polyurethane foams. They have proved to be particularly stable, giving rise in particular only to very reduced formation of 1-chloro-1-fluoroethane (HFA-151a). Such premixtures can optionally comprise one or a number of other blowing agents, in addition to the stabilized hydrofluoroalkane according to the invention. These premixtures can optionally consist only of the suitable amounts of polyol and of stabilized composition according to the invention. However, as a general rule, they comprise, besides the suitable amounts of polyol and of stabilized composition according to the invention, necessary amounts of surfactants, catalysts, flame-retardant agents and optionally other additives commonly used to prepare polyurethane foams by reacting with polyisocyanates.

The invention also relates to polyurethane or polyisocyanurate foams obtained by using a composition or a premixture in accordance with the invention, such as defined above.

Examples 2 to 9 which follow are given to illustrate the invention in a non-limiting way. Example 1(C) is given by way of reference, in the absence of stabilizing agent.

EXAMPLE 1(C)

A premixture for the preparation of polyurethane foams was prepared according to the following composition by weight:

50 parts of Arcol 3770 amino polyol from Arco
50 parts of Voranol RA 640 amino polyol from Dow
1 part of water
2 parts of B 1048 silicone surfactant from Goldschmidt
2 parts of N-methylmorpholine
1.5 parts of N,N-dimethylcyclohexylamine
24 parts of 1,1-dichloro-1-fluoroethane.

A predetermined amount of this mixture was enclosed in a glass flask maintained at a constant temperature of 50° C. for 12 days.

A sample was then withdrawn and its analysis by gas phase chromatography showed the presence of 294 mg of 1-chloro-1-fluoroethane per kg of 1,1-dichloro-1-fluoroethane.

EXAMPLE 2 to 9

Variable amounts of various stabilizing agents were added to a premixture identical to that of Example 1(C) before ageing so as to produce premixtures according to the invention.

After ageing under conditions identical to those of Example 1(C), the 1-chloro-1-fluoroethane content was measured by gas phase chromatography. The results are shown in the table below.

By comparison with Example 1(C), Examples 2 to 9 according to the invention illustrate that the amount of 1-chloro-1-fluoroethane formed is very markedly less and thus that the stability of 1,1-dichloro-1-fluoroethane is very substantially better in the premixtures according to the invention.

| Example | Stabilizing compound Nature | Amount (weight % of HFA-141b) | HFA-151a content (mg/kg HFA-141b) |
| --- | --- | --- | --- |
| 1(C) | — | — | 294 |
| 2 | 1,4-benzoquinone | 5% | <5 |
| 3 | 1,4-benzoquinone | 0.1% | <5 |
| 4 | 1,4-benzoquinone | 0.05% | 11 |
| 5 | 2-methyl-2-nitrosopropane | 5% | <5 |
| 6 | 2-methyl-2-nitrosopropane | 0.1% | <5 |
| 7 | 2-methyl-2-nitrosopropane | 0.05% | 7 |
| 8 | 2-amyltetrahydro-anthraquinone (*) | 5% | <5 |
| 9 | 2-tert-amyloctahydro-anthraquinone | 5% | <5 |

(*) mixture of tert-amyl (60%) and sec-amyl (40%) isomers

We claim:

1. A composition comprising at least one hydrofluoroalkane and at least one stabilizing agent for the hydrofluoroalkane, selected from the group consisting of quinones, compounds containing a nitroso group and mixtures thereof.

2. The composition according to claim 1, consisting essentially of said hydrofluoroalkane and said stabilizing agent.

3. The composition according to claim 1, said hydrofluoroalkane comprising 1,1-dichloro-1-fluoroethane.

4. The composition according to claim 1, wherein the quinone is selected from the group consisting of 1,4-benzoquinone, 2,6-dimethylbenzoquinone, 2-sec-amylanthraquinone, 2-tert-amylanthraquinone, 2-tert-amyltetrahydroanthraquinone and 2-tert-amyloctahydroanthraquinone.

5. The composition according to claim 1, wherein the compound containing a nitroso group is selected from the group consisting of 2-methyl-2-nitrosopropane, 2-nitroso-1-naphthol and N-nitrosodiethylamine.

6. The composition according to claim 1, including from about 0.01 to 10% by weight of each stabilizing agent with respect to the total weight of said hydrofluoroalkane.

7. In a blowing agent for the preparation of polyurethane or polyisocyanurate foam, the improvement comprising a composition according to claim 1.

* * * * *